United States Patent [19]

King, Jr.

[11] Patent Number: 5,132,447

[45] Date of Patent: Jul. 21, 1992

[54] METHOD FOR MAKING ORGANIC CARBONATES

[75] Inventor: Joseph A. King, Jr., Schenectady, N.Y.

[73] Assignee: General Electric Company, Schenectady, N.Y.

[21] Appl. No.: 724,292

[22] Filed: Jul. 1, 1991

Related U.S. Application Data

[63] Continuation of Ser. No. 503,404, Apr. 2, 1990, abandoned.

[51] Int. Cl.⁵ .................. C07C 68/00; C07C 69/96
[52] U.S. Cl. .................................. 558/274; 558/260; 558/277
[58] Field of Search .................. 558/274, 277, 260

[56] References Cited

U.S. PATENT DOCUMENTS

| | | | |
|---|---|---|---|
| 4,187,242 | 2/1980 | Chalk | 528/196 X |
| 4,260,802 | 4/1981 | Hallgren | 560/71 |
| 4,349,485 | 9/1982 | Hallgren | 260/429 X |
| 4,361,519 | 11/1982 | Hallgren | 558/277 |
| 4,410,464 | 10/1983 | Hallgren | 558/274 |

*Primary Examiner*—Vivian Garner
*Attorney, Agent, or Firm*—William A. Teoli; James C. Davis, Jr.; William H. Pittman

[57] ABSTRACT

A method is provided for making an organic carbonate such as, a diaryl carbonate by heating a mixture under elevated conditions of temperature and pressure comprising an arylhydroxy compound, such as phenol, carbon monoxide and oxygen in the presence of a palladium catalyst and carbon dioxide as a desiccant.

6 Claims, No Drawings

METHOD FOR MAKING ORGANIC CARBONATES

This application is a continuation of application Ser. No. 07/503,404, filed Apr. 2, 1990, now abandoned.

BACKGROUND OF THE INVENTION

The present invention relates to a method for making organic carbonates such as diphenyl carbonate by effecting reaction of an organic hydroxy compound, such as phenol, with carbon monoxide and oxygen in the presence of an effective amount of a palladium catalyst and carbon dioxide as a desiccant. More particularly, the present invention relates to a continuous or batch method for making organic carbonates at elevated temperatures and pressures under neat conditions in the absence of a solid desiccant.

Prior to the present invention, aromatic carbonates, such as diphenyl carbonate were made by effecting reaction between phenol, carbon monoxide, an oxidant and a Group VIII element or catalyst. Aromatic carbonates are of interest to thermoplastic manufacturers, since they offer an alternative non-phosgene route to aromatic polycarbonates by melt transesterification. A procedure for making aromatic carbonates using an organic solvent, such as, methylene chloride, is shown by Chalk, U.S. Pat. No. 4,187,242. Additional procedures for making organic carbonates are shown by Hallgren, U.S. Pat. Nos. 4,361,519 and 4,410,464, utilizing a molecular sieve as a drying agent for the water formed during the reaction. Further procedures for making aromatic carbonates by catalytic carbonylation of aromatic hydroxy compounds, are shown by Japanese patent No. 01,165,551. Reference also is made to copending applications Ser. No. 17,248, filed Jul. 11, 1988, and Ser. No. 217,257, filed Jul. 11, 1988, utilizing a divalent or trivalent manganese salt or cobalt (II) salt and hydroquinone in combination with a palladium catalyst to catalyze the conversion of an organic hydroxy compound to an organic carbonate.

Although the aforementioned methods for making organic carbonates provide effective results in particular instances, the yields of the product are often less than 10%. In addition organic solvents are generally employed as well as solid drying agents which can interfere with the recovery of catalyst values.

SUMMARY OF THE INVENTION

The present invention is based on the discovery that if carbon dioxide is initially charged under ambient conditions to the reactor along with the key ingredients used in organic carbonate production, namely the organic hydroxy compound, carbon monoxide, oxygen or air and a palladium catalyst, substantially higher yields of the organic carbonate can be obtained. Those skilled in the art know, for example, that carbon dioxide is often produced as a side product resulting from the direct combustion between carbon monoxide and oxygen during organic carbonate formation, sometimes referred to as the "burn reaction". However, as provided by the present invention, carbon dioxide can function as a desiccant if added to the reactor along with the reactants under ambient conditions, in amounts such as about 0.01 to 50 moles of carbon dioxide per mole of organic hydroxy compound. The carbon dioxide can react with the water of reaction to form carbonic acid and also minimize the burn reaction. There is also provided by the present invention the advantage of being able to introduce make-up oxygen and carbon monoxide into the reactor after they have been initially consumed, to simulate continuous conditions and achieve superior yields of organic carbonate, as compared to organic carbonate yields obtained when make-up reactants are used in methods of the prior art.

STATEMENT OF THE INVENTION

There is provided by the present invention, a method for making an organic carbonate which comprises, (1) charging a reaction vessel under ambient conditions with a mixture comprising organic hydroxy compound, carbon monoxide, an oxygen-containing gas, a catalytic amount of a palladium material, and a desiccant amount of carbon dioxide, (2) agitating the mixture of (1) at a temperature of from about 50° C. to about 170° C. and a pressure of from about 100 psi to 300 psi, and (3) recovering organic carbonate from the mixture of (2).

The organic hydroxy compound used in the practice of the invention can be selected from aliphatic, alicyclic and aromatic mono or polyhydroxy compounds, such as methanol, ethanol, butanol, cyclohexanol, phenol, cresol, xylenol, ethylene glycol, propyleneglycol, resorcinol, hydroquinone, and bisphenol A. Aromatic hydroxy compounds are particularly preferred, with phenol being the most preferred.

The palladium material or catalyst can be used in elemental form or it can be employed as a palladium compound. Accordingly, palladium black or elemental palladium deposited on carbon can be used as well as palladium compounds, such as halides, nitrates, carboxylates, and complexes involving such compounds such as carbon monoxide, amines, phosphines or olefins. The preferred palladium compounds are palladium (II) salts of organic acids including carboxylates with $C_{2-6}$ aliphatic acids. Palladium (II) acetate is particularly preferred. There also can be used in combination with palladium catalyst, tetraalkylammonium halide, such as the chlorides and bromides and particularly the bromides. Alkyl groups of the alkyl ammonium halides are primary and secondary alkyl groups containing about 1–8 carbon atoms. Tetra-n-butylammonium bromide is particularly preferred. There also can be used in combination with the palladium catalyst and the tetraalkylammonium halide at least one quinone and aromatic diol formed by the reduction of said quinone or a mixture of thereof. 1,4-quinone, 1,4-benzoquinone and hydroquinone are preferred. In addition, compounds such as 1,2-quinone and catechol, anthraquinone and 9,10-dihydroxyanthracene, tetramethyldiquinone and phenanthrenequinone also can be used.

In instances where the formation of aromatic carbonates, such as diphenyl carbonate, is desired, manganese or cobalt cocatalysts also can be used. For example, cobalt or manganese compounds such as a divalent or trivalent compounds, for example, salts such as halides and carboxylates and complexes with amines, diketones and carbon monoxide have been found effective. Cobalt (II) acetate is particularly preferred. It has been found that optimum selectivity, i.e., optimizing the formation of aromatic carbonate and minimizing the formation of aromatic salicylate is achieved using the cobalt (II) catalyst.

An effective amount of the palladium catalyst is, for example, an amount sufficient to provide about 1 gramatom of palladium, per 800-10,000 and preferably 5,000-10,000 moles of organic hydroxy compound. The other components of the palladium catalyst are, for example, per gram-atom of palladium, about 0.1-5.0, preferably about 0.5-1.5 gramatoms of manganese or cobalt and about 10 to 100 and preferably about 40-80 moles of the tetraalkylammonium halide and about 10-60 and preferably about 25-40 moles of quinone and/or reduction product thereof.

In the practice of the present invention, the reactants such as, the organic hydroxy compound, carbon monoxide, an oxygen-containing gas, the carbon dioxide desiccant and the palladium catalyst are initially introduced into the reactor. The resulting mixture can then be heated under sealed conditions while being agitated. The conditions of temperature and pressure have been previously cited in the Statement of the Invention. Of course, under continuous reaction conditions, any or all of the components can be further recycled depending upon the point at which the organic carbonate is recovered.

In order that those skilled in the art will be better able to practice the present invention, the following examples are given by way of illustration and not by way of limitation. All parts are by weight unless otherwise indicated.

EXAMPLE 1

There was added to a Parr stirred pressure reactor, 76.06 grams of phenol, 1.896 grams of diphenyl ether, 0.33 gram benzoquinone, 0.042 gram palladium diacetate, 0.035 gram of anhydrous cobalt diacetate, and 2.49 grams of tetrabutylammonium bromide. The reactor vessel was sealed, purged 4 times with $CO_2$ at 400 psi and then charged with 0.278 mole of carbon dioxide, 0.209 mole of oxygen and 0.417 mole of carbon monoxide at room temperature. The resulting partial pressures of carbon dioxide were 400 psi, oxygen 300 psi, and carbon monoxide 600 psi. The mixture was heated to 100° C. while it was stirred rapidly to ensure efficient aeration of the solution phase. After 2 hours, 7.3 grams of diphenyl carbonate (8.4% yield based on phenol) had been produced. A total internal pressure drop of 195 psi was also observed during the first 2 hours. The reactor was exhausted to 1000 psi and then recharged with 300 psi of oxygen and 620 psi of carbon monoxide. An aliquot of the mixture was removed after 3 hours following the initiation of the reaction and it was found that 9.25 grams of diphenyl carbonate (10.7% yield) had formed based on GC. At the termination of the reaction which lasted 5 hours, a total of 13.2 grams of diphenyl carbonate (15.2% yield) had been formed. Recovery of the diphenyl carbonate is readily achieved by stripping the mixture to dryness at about 19 torr and 150°-190° C. followed by distillation at about 15 torr and 200° C.

EXAMPLE 2

The procedure of Example 1 was repeated except there was utilized 50.5 gram of phenol, 4.46 grams of diphenylether, 0.275 grams of benzoquinone. 1.5 grams of tetrabutylammonium bromide, 0.062 gram of palladium diacetate, and 0.042 gram of cobalt diacetate. The reactor vessel was then again sealed and purged with 4 times 600 psi of carbon dioxide. The reaction vessel was then charged with 620 psi of carbon dioxide (0.431 mole), 380 psi of oxygen and 800 of psi of carbon monoxide, to provide a total pressure at room temperature of about 1800 psi. The reactor was then heated to 100° C. After one hour, the reactor was depressurized to 1000 psi and then recharged with 380 psi of oxygen and 760 psi of carbon monoxide to produce a total pressure of 2140 psi. After 2 hours of reaction, the reaction vessel was exhausted to 900 psi then repressurized with 450 psi of oxygen and 700 psi of carbon monoxide to provide a total pressure at 100° C. of 2050 psi. The reactor was then allowed to cool to room temperature after 3 hours of reaction. There was obtained 10.9 grams of diphenyl carbonate or a 19% yield.

EXAMPLE 3

Procedure of Example 1 was repeated except there was utilized 50.1 grams of phenol, 6.281 grams of diphenyl ether, 1.955 grams of benzoquinone, 1.5 gram of tetraabutylammonium bromide, 0.060 of palladium (II) acetate and 0.032 gram of cobalt (II) acetate. The reactor was sealed and pressurized with 400 psi of oxygen, 450 psi of carbon dioxide, and 800 psi of carbon monoxide to provide a total pressure of 1650 psi at room temperature. The reactor was heated to 100° C. At 0.5 hours, the pressure of the reactor was reduced to 1200 psi and then repressurized with 400 psi of oxygen and 600 psi of carbon monoxide. After 1 hour, the pressure of the reactor was reduced to 1000 psi, then repressurized with 350 psi of oxygen and 700 psi of carbon monoxide. The aforementioned repressurizing procedure was repeated after 2 hours had elapsed. At this time, a sample of the reaction mixture showed that it contained 22% yield of diphenyl carbonate based on GC. After the reaction had been running for 5 hours the mixture showed that it contained 14.85 grams or a 26.1% yield of diphenyl carbonate.

The above procedure was repeated except that carbon dioxide was not included in the reactor when it was initially charged with oxygen and carbon monoxide. At the termination of the reaction, it was found that there was 9.79 grams of diphenyl carbonate, or a 17.2% yield based on GPC analysis.

These results show that the presence of carbon dioxide during the initial stages of the reaction period can substantially enhance the yield of diphenyl carbonate.

Although the above results are directed to only a few of the vary many variables which can be used in the practice of the method of the present invention, it should be understood that the present invention is directed to a method for making a much broader variety of organic carbonates utilizing ingredients as set forth in the description preceding these examples.

What is claimed is:

1. A method for making an organic carbonate which comprises,
    (1) charging a reactor at ambient temperatures with a mixture comprising phenol, carbon monoxide, an oxygen containing gas, a catalytic amount of a palladium material, and from about 0.01 to 50 moles of carbon dioxide per mole of phenol.
    (2) agitating the mixture of (1) at a temperature of from about 50° C. to about 170° C. and a pressure of from about 100 psi to 3000 psi, and
    (3) recovering diphenyl carbonate from the mixture of (2).

2. A method in accordance with claim 1, where the palladium catalyst is palladium (II) acetate.

3. A method in accordance with claim 1, where the palladium catalyst is palladium (II) acetate and is used in combination with cobalt (II) diacetate as a cocatalyst.

4. A method in accordance with claim 1, where air is used as the oxygen-containing gas.

5. A method in accordance with claim 1, which is operated under continuous conditions.

6. A method in accordance with claim 1, which is operated under batch conditions.

* * * * *

United States Patent [19]

Schaeffer

[11] Patent Number: 5,132,448

[45] Date of Patent: Jul. 21, 1992

[54] PREPARATION OF ALPHA-CHLORO PHOSPHORUS YLIDES

[75] Inventor: Bernd Schaeffer, Dierbach, Fed. Rep. of Germany

[73] Assignee: BASF Aktiengesellschaft, Ludwigshafen, Fed. Rep. of Germany

[21] Appl. No.: 580,857

[22] Filed: Sep. 11, 1990

[30] Foreign Application Priority Data

Sep. 30, 1989 [DE] Fed. Rep. of Germany ....... 3932748

[51] Int. Cl.$^5$ .................... C07B 39/00; C07C 255/10
[52] U.S. Cl. ..................................... 558/385; 564/15; 568/13; 568/16
[58] Field of Search .................... 568/13, 16; 558/385; 564/15

[56] References Cited

PUBLICATIONS

Topics in Stereochemistry, vol. 5, Wiley-Interscience, Editors Eliel et al., Schlosser.
The Condensed Chemical Dictionary, Seventh Ed., Reinhold Publishing Corp.
Hackh's Chemical Dictionary, 1953, Third Edition.
Chambers Science and Technology Dictionary.
Topics in Phosphorus Chemistry vol. 5: P$^{31}$ Nuclear Magnetic Resonance, Crutchfield et al., Interscience Publishers.
Chem. Ber., 90 (1962) 3303, Märkl.
Bestmann et al., Synthesis, (1970) 590.
Denney et al., J. Org. Chem. 27 (1962) 998.

Primary Examiner—Joseph Paul Brust
Assistant Examiner—M. S. H. Gabilan
Attorney, Agent, or Firm—Keil & Weinkauf

[57] ABSTRACT

α-Chloro phosphorus ylides of the formula I

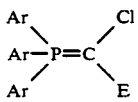    I where the Ar radicals are identical or different aryl groups, and E is a substituent which stabilizes the ylide (I), are prepared by reacting a phosphonium salt of the formula II

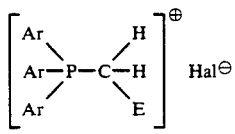    II where Hal is chlorine, bromine or iodine, with a chlorinating agent, using bleaching powder as chlorinating agent.

5 Claims, No Drawings